United States Patent [19]

Parker

[11] 4,005,700
[45] Feb. 1, 1977

[54] DEVICE FOR MEASURING BLOOD GASES

[75] Inventor: Dawood Parker, London, England

[73] Assignee: G. D. Searle & Co. Limited, Bucks, England

[22] Filed: Apr. 7, 1975

[21] Appl. No.: 566,008

[30] Foreign Application Priority Data

Apr. 5, 1974 United Kingdom ............ 15233/74

[52] U.S. Cl. .......................... 128/2 E; 128/2.1 E; 204/195 P
[51] Int. Cl.² ......................................... A61B 5/00
[58] Field of Search ................ 128/2 R, 2 E, 2.1 E, 128/2 F; 204/195 P; 356/39, 40, 41

[56] References Cited

UNITED STATES PATENTS

| | | | |
|---|---|---|---|
| 3,659,586 | 5/1972 | Johns | 128/2 E |
| 3,795,239 | 3/1974 | Eberhard | 128/2.1 E |

Primary Examiner—Richard C. Pinkham
Assistant Examiner—Marvin Siskind
Attorney, Agent, or Firm—John A. Dhuey

[57] ABSTRACT

A device for the measurement of the partial pressure of blood gases comprising a body having a gas-permeable boundary wall for placement on the skin of the subject, a gas collection chamber in the body connected to an analysis instrument, a heating device to heat the skin area under the boundary wall and an electronic control to control the heating device and monitor the temperature of the skin area.

6 Claims, 1 Drawing Figure

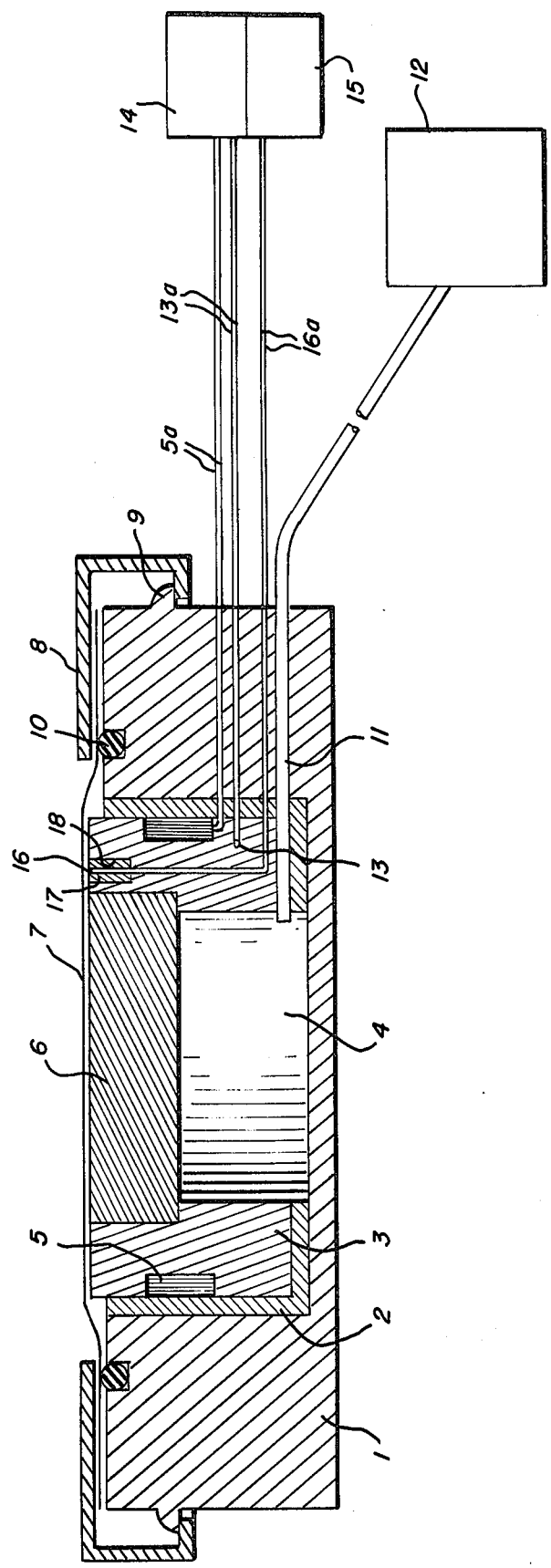

DEVICE FOR MEASURING BLOOD GASES

The present invention relates to the measurement of partial pressure of gases or vapours in the blood-stream of animals, including man and particularly, but not exclusively, to a device which may be used for the non-invasive measurement of oxygen ($PO_2$) and carbon dioxide ($PCO_2$) of arterial blood of such animals.

There are many clinical conditions in which it is necessary to monitor the partial pressure of oxygen, carbon dioxide or nitrogen or the tension of other gases in arterial blood. In particular such measurements are required during intensive care of infants or adults. Conventionally, samples of blood are taken at regular intervals and the oxygen or carbon dioxide tensions of the blood analysed by chemical or electrical means. Such method are not ideal as they either cause discomfort to the patient or require catheterisation of an artery.

More recently, it has been possible continuously to monitor the oxygen and carbon dioxide tensions of blood by means of fine measuring electrodes inserted into suitable arteries or veins. Such methods allow the constant adjustment of treatment to maintain these gas levels in the blood at the required values. However, such techniques are not satisfactory where arterial catheterisation is otherwise not justified.

An alternative known method for monitoring oxygen and carbon dioxide levels in the blood makes use of a surface electrode which is applied to the skin of the subject. The body surface of the subject is heated to stimulate blood circulation in the region to which the electrode is applied. The flow of an electric current is controlled by an electrochemical reaction, on the electrode surface, with gas which has diffused from the blood to the body surface. This current is then measured. This known method relies upon the diffusion of blood gases from the capillary circulation beneath the skin to the surface of the skin. Blood gases measured in this way will reflect gas tensions in the capillary layer beneath the skin and not arterial gas tensions. However, if the surface of the skin is heated to about 43° C or vasodilatory agents are applied to the skin, blood flow to the capillaries is increased to such an extent that little change occurs in its gas tensions due to tissue metabolism. In this way, the gas tensions measured non-invasively at the surface of the skin will reflect arterial gas tensions.

An object of the present invention is to provide an improved device which does not require arterial catheterisation and which does not involve an electrochemical reaction.

According to the present invention, there is provided a device for the measurement of the partial pressure of gases or vapours in the blood stream of animals, the said device comprising a body having a boundary wall which can be placed on the skin of an animal and an internal collecting chamber in which gases or vapours which diffuse through an area of skin defined by the boundary wall can be collected, heating means in the body operable to heat the said area of skin, and an outlet from the collecting chamber through which gases or vapours collected in the chamber can be led away to an analysis instrument. The collecting chamber may be at a reduced temperature.

Although the primary application of the device is for the measurement of blood gas levels, there are other substances which are released through the skin of a subject. These substances vapourise when subjected to the low pressure inside the collecting chamber and can be measured by a mass spectrometer. For convenience of description, such vapours will, where the context so permits hereinafter be included in the term "gases".

Since the device is capable of being placed in intimate contact with the skin and of collecting gases which diffuse through the skin within the boundaries of the device, it is essential that the boundary wall should make substantially airtight contact with the skin to isolate the interior of the device from the atmosphere, e.g. by using a double-sided adhesive ring as commonly used with E.C.G. electrodes. Gases diffusing through the skin may then collect in the collecting chamber and be led off to an analysis instrument such as a mass spectrometer. The skin contained by the boundary wall and any gas within the collecting chamber may be heated by the heating means within the boundary wall. A temperature sensing means such as a thermistor may be provided, and connected to an external unit by which the temperature may be held steady by controlling the energy applied to the heater. By heating the surface of the device in contact with the skin, the circulation of blood through the capillaries in the vicinity of the device is greatly enhanced and the oxygen tension in the tissue immediately below the surface of the skin approximates to that in the arterial blood. The presence of this high oxygen tension allows the diffusion of oxygen from the capillaries through the surface of the skin and it is this oxygen that may be collected and analysed in a mass spectrometer. The same principles apply to carbon dioxide and other gases, such as anaesthetic gases which may be dissolved in the blood of a subject. The collecting chamber of the device should have a very low volume in comparison with the surface area of skin container by it to allow small changes in gas tension to be monitored.

A membrane may be placed over the face of the device in contact with skin in order to allow selective diffusion, due to the use of a membrane having the desired permeability, of gases of interest into the collecting chamber. Such a membrance may also reduce any interference in the gas measurement which are caused by perspiration from the area of skin concerned. Gas permeable membranes, such as silicone rubber of P.T.F.E or polypropylene may be used. For example, a silicone rubber membrane is permeable to oxygen and even more so to carbon dioxide and will allow diffusion of these gases into the chamber. The collecting chamber may be filled, or partly filled with a gas-porous material such as sintered glass or sintered metal. Such a filling serves, firstly to reduce the volume of the chamber and thereby to reduce the "dead space" of the device and, secondly, to support the skin and, if present, the membrane against the suction applied by a mass spectrometer device.

It is not essential to lead the gases diffusing into the collecting chamber to a mass spectrometer, although such an instrument is preferred as it combines great sensitivity with a low requirement for gas. Furthermore, it is capable of measuring several different gases simultaneously and consequently blood-levels of these gases can be monitored simultaneously with one device. For example, a device such as the Medspect (Scientific Research Instruments) device may possibly be used.

The single figure of the accompanying drawing is a sectional diagram of a device according to one embodiment of the present invention.

The device illustrated comprises a circular disclike body 1 which may be made of any suitable materials such as aluminium, steel, nylon or other plastics. This body 1 has a central cavity or recess which has a lining 2 of a thermal insulating material which may be nylon or a ceramic. Fitted inside this is a central hollow cylindrical assembly 3 of aluminium, steel or copper. This assembly defines a central gas collecting chamber 4 and also has a peripheral recess containing an electrical heating coil 5 supplied through leads 5a. The central assembly 3 is also fitted with an internal porous support 6 which may be of sintered glass or, preferably, a porous metal such as sintered stainless steel or sintered bronze.

A gas-permeable membrane 7 is stretched across the outer surface of the porous support 6 and across the adjacent surface of the body 1 and is retained by an annular cap 8 which may be a snap fit over a retaining bead 9 on the body 1. The annular cap defines a boundary wall of the body which can be placed in contact with the skin of a patient. An O-ring 10 conveniently of neoprene, is located in a groove in the body 1 to seal the membrane 7 against the inside of the annular cap 8.

A pipe conduit 11, the wall of which is impervious to gases, leads from the interior of the collecting chamber 4 to a mass spectrometer 12 or other suitable analysis instrument capable of maintaining a gaseous partial pressure difference.

A thermistor 13 is located in the central assembly 3 and is connected to a control circuit 14 by thermister leads 13a. The leads 5a to the electrical heater 5 are also connected to the same control circuit 14 which is arranged to maintain the temperature of the body of the device in the area of contact with the skin at about 43° C.

A second thermistor 16, thermally insulated by suitable material 17 within a cavity 18 in the body 1, but having its sensing element adjacent to the membrane 7, detects the temperature of the skin of the subject and this is monitored by an indicating instrument 15 connected by thermistor leads 16a. This is very valuable when the subject to which the device is attached suffers significantly reduced peripheral perfusion when transcutaneous gas measurements may not be representative of arterial conditions, and evidence of this must be obtained to prevent incorrect administration of oxygen, for example. Under such conditions the heat carried away by the skin of the subject will be reduced due to the decrease in peripheral blood circulation and this in turn will lead to a temperature increase being indicated at the instrument 15. Such an indication will give a warning that the results produced by the spectrometer 12 are, or may be, spurious.

In use, the membrane 7 and the boundary wall defined by the surface of the cap 8 is pressed firmly against the skin of an animal in order to make the collecting chamber 4 airtight. The device is sealed on the skin of the subject as by adhesive tape. The skin of the subject and also any gas in the chamber 4, is heated by means of the passage of electric current through the heater leads 5a. The temperature achieved by such heating is detected by the thermistor 13, and controlled by the circuit 14 while the actual skin temperature is detected by the thermistor 16 and is monitored by the instrument 15. Gases diffusing through the area of skin defined by the annular cap 8 pass into the chamber 4 and are led through the conduit 11 to the analysis instrument 12. Individual gases within this gas mixture may then be analysed and changes in the proportions of different gases detected.

From these measurements it is possible to obtain a useful indication of the arterial oxygen and other gas levels and also to detect changes in the levels of these gases in the blood.

It will be appreciated that the use of an electrical resistance heater such as heater 5 is not essential, as other forms of heating may be used.

What we claim is:

1. A device for the measurement of the partial pressure of gases or vapours in the blood stream of animals, including man, said device comprising a body having a boundary wall which can be placed on the skin of an animal and an internal collecting chamber in which gases or vapours which diffuse through an area of skin defined by the boundary wall can be collected, heating means in the body operable to heat said area of skin, an outlet from the collecting chamber through which gases or vapours collected in the chamber can be led away to an analysis instrument, control means responsive to the temperature of said body of the device and operable to control said heating means, and means responsive to the temperature of the skin of the animal and connected with an indicator operable to monitor said temperature.

2. A device as claimed in claim 1, wherein the outlet is connected with a mass spectrometer which can be maintained under a gaseous partial pressure difference.

3. A device as claimed in claim 1, wherein the collecting chamber has a wall formed by a porous support for the said area of skin and through which gas or vapours can diffuse into the collecting chamber.

4. A device as claimed in claim 3 wherein a membrane permeable to gases or vapours from the subject is arranged in contact with the porous support and is retained by an annular cap fitted on the body and defining the boundary wall thereof.

5. A device as claimed in claim 1, wherein the body has a central recess lined with thermal insulation material, a central assembly is located in the recess and defines the collecting chamber, the said assembly containing an electrical heater and also having a porous support arranged so that it can be placed on the said area of skin and permitting the gases or vapours to diffuse therethrough into the collecting chamber.

6. A method of measuring the partial pressure of gases or vapours in the blood stream of animals including man comprising the steps of applying to the skin of a subject a boundary wall of a collecting device, heating an area of skin defined by the boundary wall, collecting in the collecting device gases or vapours which have diffused through the said area of skin, withdrawing the gases or vapours from the collecting device and passing them to an analysis instrument; measuring the proportions and changes in proportions of constituents of the gases or vapours; and continuously monitoring the temperature of said area of skin.

* * * * *